(12) United States Patent
Chien (10) Patent No.: US 10,722,422 B2
(45) Date of Patent: Jul. 28, 2020

(54) VISUAL ACUITY TRAINING DEVICE AND VISUAL ACUITY TRAINING METHODS

(71) Applicant: Shun-Yuan Chien, Kaohsiung (TW)

(72) Inventor: Shun-Yuan Chien, Kaohsiung (TW)

(*) Notice: Subject to any disclaimer, the term of this patent is extended or adjusted under 35 U.S.C. 154(b) by 925 days.

(21) Appl. No.: 15/353,302

(22) Filed: Nov. 16, 2016

(65) Prior Publication Data

US 2018/0098908 A1 Apr. 12, 2018

(30) Foreign Application Priority Data

Oct. 10, 2016 (CN) .......................... 2016 1 0881414

(51) Int. Cl.
*A61H 5/00* (2006.01)
*G09B 19/00* (2006.01)
*A61H 23/00* (2006.01)
*A61B 3/113* (2006.01)

(52) U.S. Cl.
CPC ............... *A61H 5/00* (2013.01); *A61H 23/00* (2013.01); *G09B 19/003* (2013.01); *A61B 3/113* (2013.01); *A61H 2230/60* (2013.01); *A61H 2230/605* (2013.01)

(58) Field of Classification Search
CPC .......... A61H 5/00; A61H 5/005; A61H 23/00; A61H 2230/60; A61H 2230/605; A61B 3/113; A61B 3/028; G09B 19/003
See application file for complete search history.

(56) References Cited

U.S. PATENT DOCUMENTS

| 2003/0056281 A1* | 3/2003 | Hasegawa | A61F 7/02 2/428 |
| 2004/0257528 A1* | 12/2004 | Miyake | A61H 5/00 351/203 |
| 2013/0057536 A1* | 3/2013 | Li | G06T 13/20 345/419 |

FOREIGN PATENT DOCUMENTS

WO WO-2016001902 A1 * 1/2016 ............. G06F 3/012

* cited by examiner

*Primary Examiner* — Valerie L Woodward
(74) *Attorney, Agent, or Firm* — Andrew M. Calderon; Roberts Calderon Safran & Cole P.C.

(57) ABSTRACT

A visual acuity (VA) training device includes a guiding unit, an eye-movement sensor, and a controller. The guiding unit is configured to guide an eyeball to move towards multiple predetermined positions. The eye-movement sensor is configured to obtain multiple eye-movement signals according to movement of the eyeball. The controller obtains multiple eyeball muscle parameters according to the eye-movement signals, and the controller controls the guiding unit according to the eyeball muscle parameters, so as to adjust the predetermined positions.

11 Claims, 4 Drawing Sheets

VISUAL ACUITY TRAINING DEVICE AND VISUAL ACUITY TRAINING METHODS

CROSS-REFERENCE TO RELATED APPLICATION

This non-provisional application claims priority under 35 U.S.C. § 119(a) to Patent Application No. 201610881414.9 filed in China, P.R.C. on Oct. 10, 2016, the entire contents of which are hereby incorporated by reference.

BACKGROUND

Technical Field

The present invention relates to a visual acuity (VA) training device and a training method thereof, and in particular, to a visual acuity (VA) training device for training eyeball muscles and a method thereof.

Related Art

Basically, the major reason for visual acuity (VA) degradation or visual fatigue is an eyeball overused or inappropriate use, resulting in that extraocular muscles and ciliary muscles are in a state of tension or spasm for a long period of time, such that the function of the extraocular muscles and ciliary muscles for regulating the eyeball declines.

In view of the increasing emphasis on the visual acuity (VA) health care issue, most people perform visual acuity (VA) screening and training with the aid of ophthalmologists. Generally, the currently existing visual acuity (VA) training instruments are commonly used by the general public. The visual acuity (VA) trainings of the visual acuity (VA) training instruments are usually in unified mode, and there is not customized visual acuity (VA) training. However, the visual acuity (VA) situation of each person is inherently different, and visual acuity (VA) training needs to be continuously monitored. The visual acuity (VA) of a same individual may even differ at different time points with different degrees of use. That is, there are different test results at different time points for the same individual in different physiological states. Thus, the existing visual acuity (VA) training device and visual acuity (VA) training method cannot perform fine-tuning based on individual visual acuity (VA) changes and cannot be specifically adjusted with respect to the visual acuity (VA) situation of each person.

SUMMARY

An embodiment of the present invention provides an visual acuity (VA) training device, where the visual acuity (VA) training device includes a guiding unit, an eye-movement sensor, and a controller. The guiding unit is configured to guide an eyeball to move towards multiple predetermined positions. The eye-movement sensor is configured to obtain multiple eye-movement signals according to movement of the eyeball. The controller obtains multiple eyeball muscle parameters according to the eye-movement signals, and the controller controls the guiding unit according to the eyeball muscle parameters, so as to adjust the predetermined positions.

The present invention provides a visual acuity (VA) training method. The visual acuity (VA) training method includes: providing, in a visible region, a visible target object according to a dynamic parameter; sensing movement of the eyeball, so as to obtain an eye-movement signal; obtaining multiple eyeball muscle parameters according to the eye-movement signal; obtaining multiple eyeball muscle parameters according to multiple eye-movement signals; and adjusting the dynamic parameter according to the eyeball muscle parameters.

In view of the above, the embodiments of the present invention provide a visual acuity (VA) training device and a training method thereof. The visual acuity (VA) training device includes a guiding unit, an eye-movement sensor, and a controller. An eyeball of a user moves towards multiple predetermined positions along with a visible target object of the guiding unit. The eye-movement sensor senses movement of the eyeball, so as to obtain multiple eye-movement signals. The controller calculates to obtain multiple corresponding eyeball muscle parameters based on the eye-movement signals.

A difference between the movement state of at least one eyeball of a user and the normal state indicates that the movement of ocular muscles of the eyeball is unbalanced. Specifically, the controller determines whether the movement of ocular muscles at a current time point is unbalanced by comparing an eyeball muscle parameter obtained at the current time point with a historical basic value. If the compared result between the eyeball muscle parameter obtained at the current time point and the historical basic value is greater than or less than a threshold or does not fall within a preset interval of the historical basic value (or referred to as a normal interval), it indicates that the movement of the eyeball at the time point corresponding to the compared result is abnormal as compared with the movement of the eyeball at previous time points. On the basis of this, the controller can carry out training with respect to unbalanced ocular muscles of the eyeball by adjusting the dynamic parameter of the visible target object. By the visual acuity (VA) training device and the visual acuity (VA) training method provided by the embodiments of the present invention, movement of ocular muscles can be adjusted with respect to a visual acuity (VA) situation of each person by changing predetermined positions of a visible target object in response to an individual visual acuity (VA) change.

DETAILED DESCRIPTION

Figure 1A:
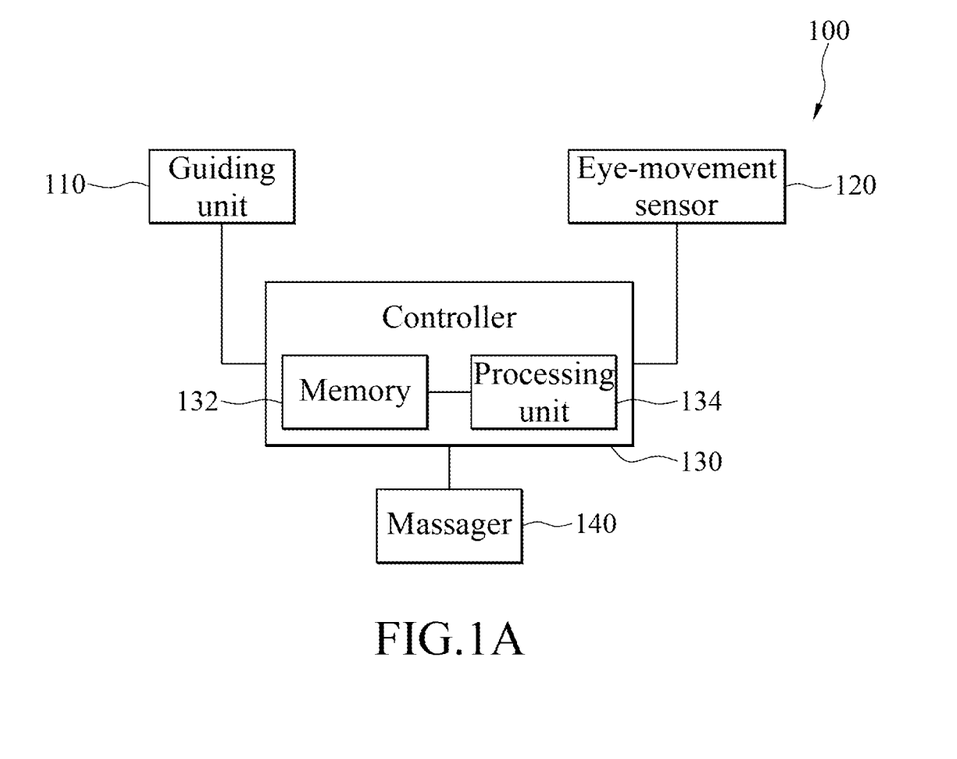
FIG. 1A is a schematic block diagram of a circuit of a visual acuity (VA) training device according to an embodiment of the present invention.
Figure 1B:
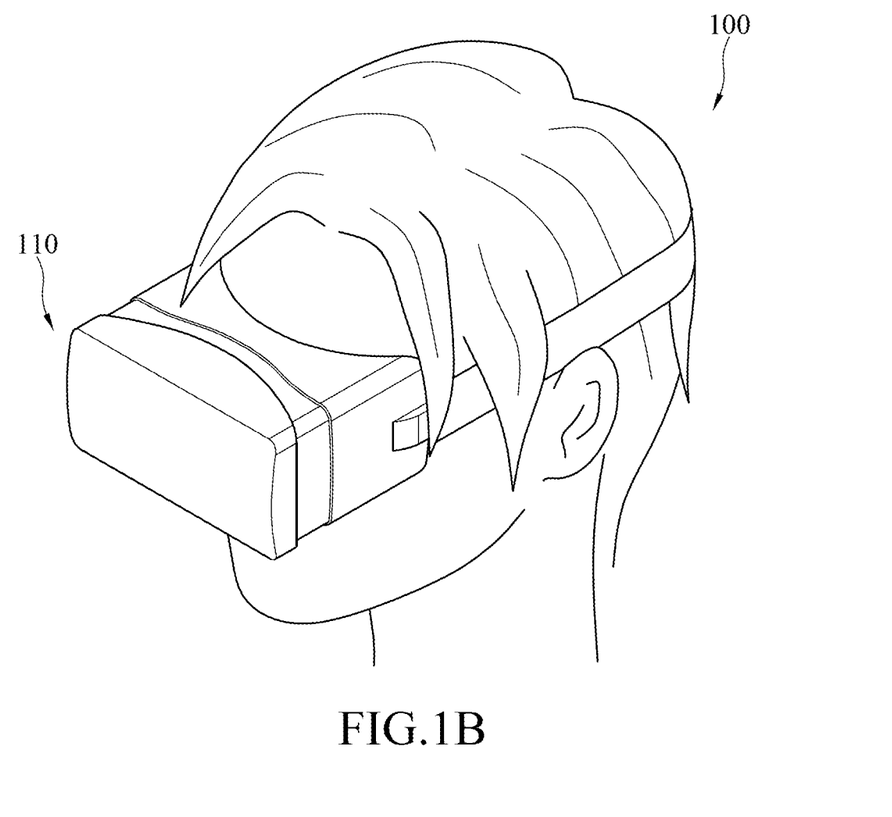
FIG. 1B is a schematic structural diagram of a visual acuity (VA) training device according to an embodiment of the present invention.

FIG. 1A is a schematic block diagram of a circuit of a visual acuity (VA) training device according to an embodiment of the present invention. FIG. 1B is a schematic structural diagram of a visual acuity (VA) training device according to an embodiment of the present invention. FIG.

Figure 2A:
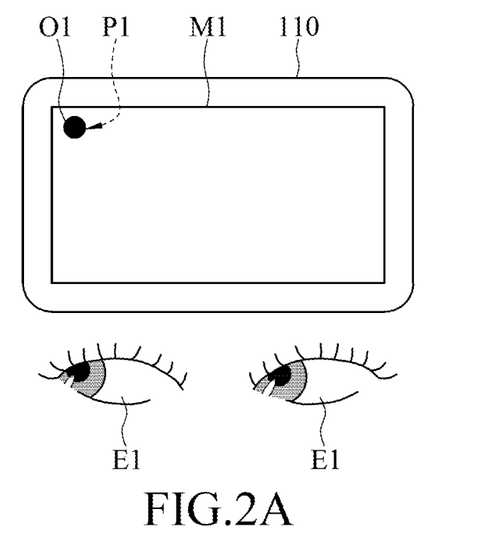
FIG. 2A to FIG. 2D are schematic diagrams showing states in which a guiding unit provides, in a visible region, a visible target object at multiple predetermined positions according to a dynamic parameter for being viewed by an eyeball according to an embodiment of the present invention.
Figure 2B:
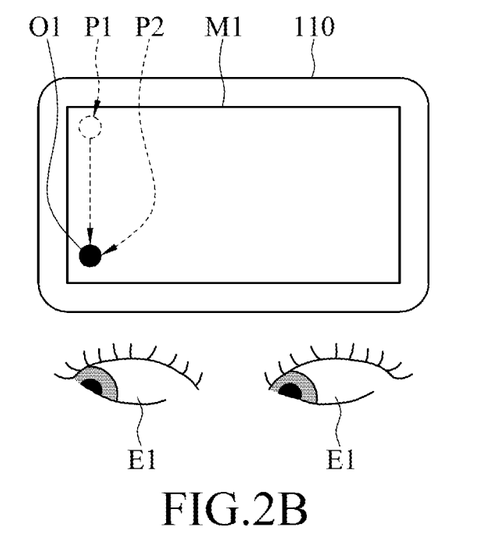
Figure 2C:
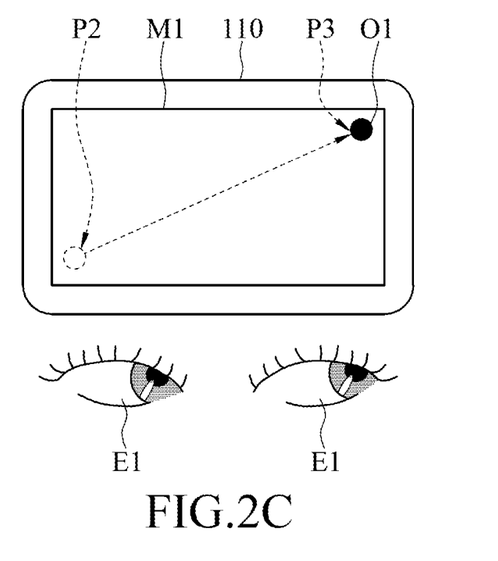
Figure 2D:
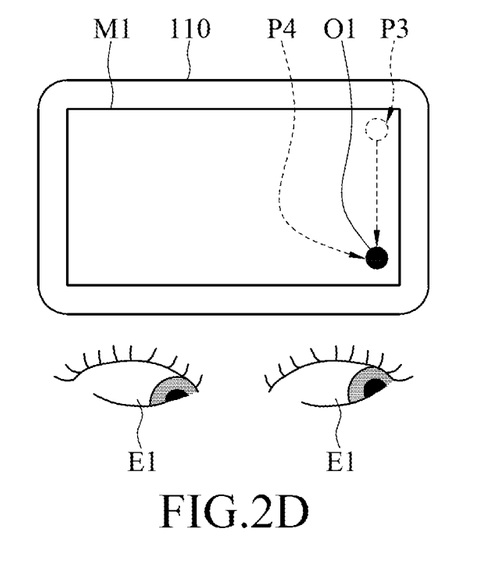

2A to FIG. 2D are schematic diagrams showing states in which a guiding unit provides, in a visible region, a visible target object at multiple predetermined positions according to a dynamic parameter for being viewed by an eyeball according to an embodiment of the present invention. Referring to FIG. 1A, FIG. 1B, and FIG. 2A to FIG. 2D, the visual acuity (VA) training device 100 includes a guiding unit 110, an eye-movement sensor 120, and a controller 130. The guiding unit 110 guides the eyeball E1 to move towards predetermined positions P1, P2, P3, P4, and the eye-movement sensor 120 obtains an eye-movement signal according to movement of the eyeball E1. The controller 130 obtains an eyeball muscle parameter according to the eye-movement signal, and controls the guiding unit 110 according to whether the eyeball muscle parameter is abnormal, so as to adjust the predetermined positions P1, P2, P3, P4, and to guide the eyeball E1 based on the adjusted predetermined positions P1, P2, P3, P4.

The guiding unit 110 is configured to guide the eyeball E1 of a user, such that the eyeball E1 of a user can move towards multiple predetermined positions. For example, the guiding unit 110 is adapted to provide, in a visible region M1, a visible target object O1 based on a dynamic parameter for the eyeball E1 to rotate or adjust the focal distance for viewing the visible target object O1, such that the eyeball E1 is further enabled to generate a movement vector.

The guiding unit 110 may be a guiding system, such as, but is not limited to, a carrier for displaying the visible target object O1, such as a display, a television, a virtual reality (VR) device, an augmented reality (AR) device, or a mixed reality (MR). The visible region M1 refers to a region that is viewable by the eyeball E1 of the user, and the visible region M1 may display a visible target object O1 for being viewed by the eyeball E1. The visible region M1 may be, but is not limited to, a screen, a white board, virtual reality glasses, or the like provided for the guiding unit 110. The dynamic parameter may be, but is not limited to, a movement vector, a distance, a focal distance, a movement track, discontinuous positions, relative coordinates, or absolute coordinates. The visible target object O1 is a target for being viewed by the eyeball E1, which may be, but is not limited to, an entity, a virtual image, or the like. For example, the dynamic parameter is a continuous movement track, and a movement vector that moves by 10 centimeters at a rate of one millimeter per second directly to the bottom is used as an instance. The visible target object O1 moves by 10 centimeters, from the position within the visible region M1 at the current time point, at the rate of one millimeter per second directly to the bottom.

In an embodiment, as shown in FIG. 1B, provided is one of the implementation manners. The visual acuity (VA) training device 100 may be a device having a virtual reality function, the guiding unit 110 may be glasses having a virtual reality function, and the eye-movement sensor 120 and the controller 130 may be combined in or built in a frame of the glasses (not shown). In this embodiment, the visible region M1 is virtual reality glasses of a virtual reality environment, and the visible target object O1 may be a virtual image displayed in the virtual reality environment. For example, the visible target object O1 may be virtual images of various types such as a baseball, a frisbee, or the like, flying over to the user. When the user wears the guiding unit 110, the eyeball E1 can view the visible target object O1 that moves along with the dynamic parameter and the eyeball E1 generates eyeball movement along with the movement of the visible target object O1, such that the visible target object O1 can guide the eyeball E1 to move towards the predetermined positions.

It should be noted that the eyeball movement may be, but is not limited to, gazing, moving, rotating, adjusting focal distance, saccading, or a combination of at least two of the above. According to the eyeball movement, information such as the movement velocity, the movement direction, the angular velocity of rotation, the focal distance value, the stretching contraction of the ocular muscles, the nystagmus, the time of saccade, or the amplitude of the saccade of the eyeball E1 can be obtained.

For example, as shown in FIG. 2A to FIG. 2D, the visible target object O1 is displayed in the visible region M1 and moves towards multiple predetermined positions P1, P2, P3, P4 at different time points. The predetermined positions P1, P2, P3, P4 may be the same position or different positions. As shown in FIG. 2A, at a first time point, the visible target object O1 is located at the predetermined position P1 firstly and the eyeball E1 is able to view the visible target object O1 at the predetermined position P1. Subsequently, as shown in FIG. 2B, at a second time point, the visible target object O1 is moved from the predetermined position P1 to the predetermined position P2, at which time the eyeball E1 moves from the predetermined position P1 to the predetermined position P2 for viewing the visible target object O1. By parity of reasoning, as shown in FIG. 2C and FIG. 2D, at a third time point and a fourth time point, the visible target object O1 is sequentially moved from the predetermined position P2 to the predetermined position P3, and then moved from the predetermined position P3 to the predetermined position P4. It should be noted that the visible target object O1 is moved along at least one track (for example, the dummy lines shown in FIG. 2A to FIG. 2D), so as to guide the eyeball E1 to move for sequentially observing the visible target object O1 located at the predetermined positions P1, P2, P3, P4. Although a straight line is used as an example of the foregoing track, the present invention is not limited thereto, and any track from one predetermined position to another predetermined position is an implementable manner, for example, but not limited to, tracks such as a curve, an arc, or a reciprocating polygonal line.

The eye-movement sensor 120 is configured to sense movement of the eyeball E1 of the user and to obtain an eye-movement signal according to the movement of the eyeball E1. It should be noted that the eye-movement sensor 120 may sense two eyeballs E1 of the user simultaneously, or may also sense only one of the eyeballs E1 of the user. Therefore, the eye-movement signal may be either two eye-movement signals of the two eyeballs of the user or one eye-movement signal of only one of the eyeballs of the user.

In practice, the eye-movement sensor 120 may sense movement of the eyeball E1 through different principles. The eye-movement sensor 120 may be an eye-movement sensoring system, such as, but not limited to, electroencephalography (EEG), electro-oculogram (EOG), electromyography (EMG), eye movement tracking device, or the like, to detect the movement track of the eyeball E1. Alternatively, the eye-movement sensor 120 may also be a camera. An image of the movement of the eyeball E1 is captured by directly filming the movement of the eyeball E1 of the user using the camera, and the image is analyzed to obtain an eye-movement signal corresponding to the movement of the eyeball E1.

The eyeball E1 is controlled by the ocular muscles to generate movement, for viewing the visible target object O1. The ocular muscles of each eyeball E1 include at least six extraocular muscles and a circular ciliary muscle. The extraocular muscles include superior rectus muscle, inferior rectus muscle, medial rectus muscle, lateral rectus muscle, superior oblique muscle, and inferior oblique muscle. The six extraocular muscles coordinate and cooperate, can enable the eyeball E1 to rotate in any direction, so as to allow the eyeball to watch a target. In addition, a crystalline lens of the eyeball E1 is adjusted by means of the surrounding ciliary muscle, so that the eyeball E1 can adjust the focal distance for viewing. When the eyeball E1 of the user is focused on the visible target object O1 and moves therewith, the eyeball E1 needs to coordinate at least through the ocular muscles, so that the eyeball E1 can generate eyeball movement with a displacement of the visible target object O1. The eye-movement sensor 120 senses the eyeball movement to obtain an eye-movement signal. The eye-movement signal may include at least eye-movement signals of multiple ocular muscles (including eye-movement signals such as stretching, contraction, and nystagmus of the respective ocular muscles), or an eye-movement signal of only one of the muscles, an eye-movement signal of eyeball movement velocity, an eye-movement signal of eyeball movement accelerated velocity, an eye-movement signal of eyeball movement angular velocity, an eye-movement signal of an eyeball focal distance value, an eye-movement signal of eyeball saccade (including at least eye-movement signals such as saccade time and saccade amplitude), or the like.

For example, as shown in FIG. 2A to FIG. 2D, the right eyeball E1 may be masked depending on the circumstances (the masked state is not shown), and the instance in which only the left eyeball of the user is sensed is used as an example. As shown in FIG. 2A, at a first time point, the visible target object O1 is located at the predetermined position P1 firstly and the left eyeball E1 views the visible target object O1 at the predetermined position P1. At this time, the superior rectus muscle and the lateral rectus muscle of the left eyeball contract, and the eye-movement signals obtained by the eye-movement sensor 120 include at least an eye-movement signal of superior rectus muscle contraction and an eye-movement signal of the lateral rectus muscle contraction of the left eyeball. Subsequently, as shown in FIG. 2B, at a second time point, the visible target object O1 is moved from the predetermined position P1 to the predetermined position P2, at which time the left eyeball moves from the predetermined position P1 to the predetermined position P2 for viewing the visible target object O1. At this time, the inferior rectus muscle and the lateral rectus muscle of the left eyeball contract, and the eye-movement signals obtained by the eye-movement sensor 120 include at least an eye-movement signal of inferior rectus muscle contraction and an eye-movement signal of the lateral rectus muscle contraction of the left eyeball. By parity of reasoning, as shown in FIG. 2C and FIG. 2D, at a third time point and a fourth time point, the eye-movement sensor 120 can sequentially obtain the eye-movement signals of the left eyeball corresponding to the predetermined position P3 and the predetermined position P4.

In other embodiments, the visible target object O1 may also generate a near-far distance change (not shown) according to different dynamic parameters, so that the eye-movement sensor 120 can obtain an eye-movement signal of an eyeball focal distance value or an eye-movement signal of the ciliary muscle by sensing the eyeball E1. It should be noted that the visible target object O1 may vary according to different dynamic parameters, such as displacement or distance, so as to enable the eye-movement sensor 120 to obtain more corresponding eye-movement signals by sensing the eyeball E1.

The controller 130 receives multiple eye-movement signals from the eye-movement sensor 120, obtains an eyeball muscle parameter corresponding to each eye-movement signal, and controls the guiding unit 110 according to the eyeball muscle parameters to adjust the predetermined positions of the visible target object O1. It should be noted that the eye-movement signal sensed at each time point corresponds to at least eyeball muscle parameters of one or more ocular muscles of the eyeball at the time point. Specifically, the eyeball muscle parameters of each ocular muscle can be, but is not limited to, the degree of stretching or contraction of the ocular muscle, the amplitude and frequency of ocular muscle nystagmus, the angular velocity of eyeball rotation, the eyeball focal distance value, the time and amplitude of eyeball saccade, or the like.

In practice, the controller 130 includes a memory 132 and a processing unit 134. The processing unit 134 may be, but is not limited to, a digital signal processor (DSP) or a central processing unit (CPU). The memory 132 may be any memory built in the controller 130 or external to the controller 130. In this embodiment, the memory 132 is a built-in memory, and the memory may store an eyeball muscle parameter or an eye-movement signal at each time point obtained by the controller 130, or may also store a data table (or referred to as a lookup table). The processing unit 134 may analyze and calculate, according to the eyeball muscle parameter or the eye-movement signal, to obtain an ocular muscle corresponding to movement of the eyeball E1 and a movement parameter of the ocular muscle. In this embodiment, the processing unit 134 may receive the eye-movement signal, obtain eyeball muscle parameters of one or multiple ocular muscles of the eyeball E1 by querying the data table in the memory 132, or by directly analyzing the eye-movement signal, and transfer the eyeball muscle parameters to memory 132 for storage. The memory 132 may be configured to store a data table and an eye-movement signal from the eye-movement sensor 120.

In addition, in other embodiments, the eye-movement sensor 120 may also convert the eye-movement signals into eyeball muscle parameters and then transmit the eyeball muscle parameters to the controller 130. Therefore, the controller 130 may directly obtain the eyeball muscle parameters from the eye-movement sensor 120 and transfer the eyeball muscle parameters to the memory 132 for storage.

For example, as shown in FIG. 2A, if the eye-movement signal is a movement velocity of the left eyeball to the upper left, the processing unit 134 may obtain respective degrees of contraction and stretching of six extraocular muscles of the left eyeball by table querying or by analyzing, or may obtain only degrees of contraction and stretching of the superior rectus muscle and the lateral rectus muscle of the left eyeball. By parity of reasoning, as shown in FIG. 2B, FIG. 2C, and FIG. 2D, the processing unit 134 may sequentially obtain eyeball muscle parameters corresponding to the left eyeball at the second, third, and fourth time points.

In other embodiments, the visible target object O1 may also move to the upper left and change the near and far distances (not shown), and therefore the eye-movement signal may also include eye-movement signals of a movement velocity of the left eyeball to the upper left and a focal distance value of the left eyeball. Accordingly, the controller 130 may obtain degrees of contraction and stretching of the six respective extraocular muscles or of only the superior rectus muscle and the lateral rectus muscle, degrees of contraction and stretching of the ciliary muscle, and a focal distance value change, of the left eyeball.

Basically, when the eyeball E1 of the user is focused on the visible target object O1 and moves therewith, the ocular muscles of the eyeball E1 need to be coordinated and the movement needs to be balanced. Accordingly, normal eyeball movement is defined as the balance of movement of the extraocular muscles and ciliary muscle of the eyeball E1 when the eyeball E1 follows the movement of the visible target object O1. It should be noted that unbalanced ocular muscle movement of the eyeball E1 at a certain time point indicates that the movement state of the eyeball E1 of the user is different from the normal eyeball movement, that is, defined as abnormal eyeball movement.

The controller 130 obtains a compared result by comparing an eyeball muscle parameter obtained at a current time point with a historical basic value of eyeball muscle parameters obtained at previous time points, to determine whether movement of the ocular muscles at the current time point is unbalanced. If the compared result between the eyeball muscle parameter obtained at the current time point and the historical basic value is greater than or less than a threshold or does not fall within a preset interval of the historical basic value, it indicates that the movement of the eyeball at the time point corresponding to the compared result is abnormal as compared with the movement of the eyeball at the previous time points. Accordingly, the processing unit can determine that the ocular muscles of the eyeball are unbalanced, and can train the unbalanced ocular muscles of the eyeball by adjusting the dynamic parameter of the visible target object O1.

It should be noted that the current time point is the latest time point when the user uses the visual acuity (VA) training device 100, and the previous time point is an earlier time point with respect to the current time point. The historical basic value may be, but is not limited to, an average of at least some of or all of the eyeball muscle parameters obtained at the previous time points. The processing unit 134 can perform calculation by selecting only eyeball muscle parameters at multiple previous time points closest to the current time point instead of selecting all the eyeball muscle parameters of the previous times point when calculating a historical basic value of some of the eyeball muscle parameters obtained at the previous time points. For example, if the eyeball E1 of the user moves ten consecutive times (the first to the tenth) along with the visible target object O1, the processing unit 134 may calculate a historical basic value based on eyeball muscle parameters measured at the five time points (that is, the sixth to the tenth) closest to the current time point. However, in other embodiments, the processing unit 134 may also calculate the historical basic value of the eyeball muscle parameters for all ten measurements.

The average may be an average of at least some of or all of eyeball muscle parameters obtained at the previous time points calculated by using methods such as an arithmetic-average method, a weighted-average method, a weighted moving average method, or an artificial intelligence algorithm.

The comparison value may be a difference obtained by subtracting the eyeball muscle parameter obtained at each current time point from the historical basic value. Alternatively, the comparison value may also be a ratio obtained by dividing the eyeball muscle parameter obtained at each current time point by the historical basic value. Alternatively, the comparison value may also be a standard deviation obtained by calculating the square root of an average of the sum of the squares of differences between respective current eyeball muscle parameters obtained at each current time point and the historical basic value (deviation from average).

If the compared result between the eyeball muscle parameter obtained at the current time point and the historical basic value is greater than or less than a threshold or does not fall within a preset interval of the historical basic value, the processing unit 134 determines that the movement of the eyeball at the time point corresponding to the compared result is abnormal as compared with the movement of the eyeball at the previous time points.

The threshold may be a preset threshold value, a percentage value, or the like. For example, whether a difference obtained by subtracting the eyeball muscle parameter obtained at each current time point from the historical basic value is greater or less than a preset threshold value is determined. Alternatively, whether a ratio obtained by dividing the eyeball muscle parameter obtained at each current time point by the historical basic value is greater or less than a preset percentage value is determined.

In addition, the preset interval may be the historical basic value plus/minus once, twice, or triple of the standard deviation, and if the eyeball muscle parameter obtained at the current time point does not fall within the preset interval of the historical basic value, it indicates that movement of muscles corresponding to the eyeball muscle parameter obtained at the current time point is probably abnormal. To further illustrate whether the current muscle parameter falls within a preset interval of the historical basic value, one parameter of one muscle is used as an example below. For example, the obtained eyeball muscle parameter is a contraction velocity of the superior rectus muscle of the left eye, and ten historical eyeball muscle parameters, namely, 10.2, 9.8, 8.9, 9.7, 10.3, 10.8, 11.1, 10.4, 9.5, 9.9 (the unit is omitted), are obtained in a chronological order, the historical basic value (the average) of the latest ten historical eyeball muscle parameters is 10.06, and the standard deviation is 0.6415. If the average plus twice of the standard deviation is used as the preset interval, the interval is (8.777, 11.343). Accordingly, if the eyeball muscle parameter obtained at the current time point (the eleventh time) is 11.4, which does not fall within the preset interval, it is judged to be abnormal. If the eyeball muscle parameter obtained at the current time point is 10.9, which falls within the preset interval, it is judged to be normal. If the currently obtained muscle parameter is 8.6, which does not fall within the preset interval, it is judged to be abnormal.

The compared result is determined based on being greater than or less than a threshold, depending on the type of the eyeball muscle parameter. For example, if the eyeball muscle parameter is the time and amplitude of eyeball saccade, the condition is set as being greater than a threshold. If the eyeball muscle parameter is a degree of stretching or contraction of an ocular muscle, the condition is set as being less than a threshold.

Certainly, in this embodiment, the abnormality is determined as long as one compared result does not fall within the preset interval. However, in practice, alternatively, the abnormality is determined when all successive compared results do not fall within the present interval.

When the processing unit 134 determines that the eyeball movement at the time point corresponding to the compared result is abnormal, the processing unit 134 may accordingly adjust the dynamic target of the visible target object O1 according to the eyeball muscle parameter at the time point corresponding to the compared result, to further enable the guiding unit 110 to adjust the predetermined positions P1, P2, P3, P4, and to guide the eyeball E1 based on the adjusted predetermined positions P1, P2, P3, P4, thereby intensively training an unbalanced extraocular muscle. In an embodiment, the dynamic parameter or default position may be adjusted when abnormality appears the first time among the respective compared results, such that the visible target object O1 can subsequently guide the eyeball to move in a manner of testing a possibly abnormal muscle, so as to obtain information about whether a muscle is abnormal more rapidly. However, in other embodiments, alternatively, the dynamic parameter or default position is adjusted when abnormality appears in successive compared results, so that the visible target object O1 subsequently guides in a manner of testing a possibly abnormal muscle. It should be noted that the adjusted predetermined positions can refer to, but are not limited to, that the visible target object O1 appears in a series of predetermined positions, and residence periods of time of the visible target object O1 at the respective predetermined positions, a movement velocity and path of the visible target object O1 are all associated with courses in respect of which an abnormal muscle, of a user, to be trained.

For example, as shown in FIG. 2A to FIG. 2D, the right eyeball E1 may be masked depending on the circumstances (not shown), and the instance in which only the left eyeball of the user is sensed is used as an example. Referring to FIG. 2A to FIG. 2D, from a first time point to a fourth time point, the left eyeball is sequentially moved from the predetermined position P1 to the predetermined position P4 along with the visible target object O1. The processing unit 134 may compare an eyeball muscle parameter measured at the fourth time point (that is, the current time point) with a historical basic value of eyeball muscle parameters measured at the first time point to the third time point (that is, the previous time points), to obtain a compared result. As shown in FIG. 2D, if the compared result between the eyeball muscle parameter obtained at the fourth time point and historical basic value is greater than or less than a threshold or does not fall within a preset interval of the historical basic value, the processing unit 134 determines that the eyeball movement corresponding to the fourth time point is abnormal as compared to the eyeball movement at the first to third points, and it can be known from the eyeball muscle parameter corresponding to the fourth time point that the amount of contraction of the superior oblique muscle and the medial rectus muscle of the left eyeball is relatively small. Accordingly, the processing unit 134 can adjust the dynamic parameter to intensively train the unbalanced extraocular muscles. Specifically, as shown in FIG. 2D, if the processing unit 134 determines that the amount of contraction of the superior oblique and medial rectus muscle of the left eyeball is small, the processing unit 134 accordingly adjusts the dynamic parameter of the visible target object O1, so that the visible target object O1 is moved to the lower left. The left eyeball can moves intuitively with the visible target object O1 and looks towards the lower left, so as to train the superior oblique and medial rectus muscle of the left eyeball.

In addition, the processing unit 134 may also adjust the appearance frequency or movement velocity, track, and distance of the visible target object O1, such as, but not limited to, the visible target object O1 may continuingly guide the eyeball E1 or continuously guide the eyeball E1 for multiple times at a specific frequency, so that the user intently trains the muscle to be trained by observing the visible target object O1. In addition, in other embodiments, the eye-movement sensor 120 can also simultaneously sense two eyeballs E1 of the same user, and therefore the eye-movement sensor 120 can synchronously or non-synchronously detect and train unbalanced extraocular muscles of the two eyeballs.

In an embodiment, the controller 130 can also know the training situation of the eyeball E1 by receiving the eye-movement signal from the eye-movement sensor 120, so as to monitor whether the eyeball E1 moves along with the visible target object O1 to receive training.

After determining a specific muscle to be trained, there may be a corresponding training course for a specific incongruous item corresponding to the muscle, but there may also be no corresponding training course. No matter whether there is a corresponding training course, the focus of the training is to make the specific muscle move. By using muscle contraction inconsistency as an example, the movement may include, but is not limited to, different strokes of contraction and/or stretching, frequency of contraction and/or stretching, velocity of contraction and/or stretching, and the like.

When the compared result between the respective eyeball muscle parameter and a historical basic value of some of the eyeball muscle parameters calculated by the processing unit 134 is gradually increased, the processing unit 134 determines that visual fatigue occurs in the eyeball E1. In detail, the amplitude of saccade, the frequency of saccade, or the time needed for saccade is related to the balance of the extraocular muscles. When the visual fatigue occurs in the eyeball E1, the amplitude of saccade is increased and the needed time is prolonged. That is, under the guide of the same displacement and frequency of the visible target object O1, the obtained rotation angular velocity of the eyeball E1 is gradually slowed down and the frequency of saccade is reduced, and therefore the unbalance amplitude of the extraocular muscles may be increased. The gradual increase in the compared value between the eyeball muscle parameter obtained at the current time point and a historical basic value of some of multiple eyeball muscle parameters obtained at previous time points calculated by the processing unit 134 indicates that the movement velocity or the movement direction of the eyeball E1 is gradually out of step with the movement velocity or the movement direction of the visible target object O1. Accordingly, the processing unit 134 determines that visual fatigue occurs in the eyeball E1.

The visual acuity (VA) training device 100 may further include a massager 140. The massager 140 is electrically connected to the controller 130. When the processing unit 134 of the controller 130 determines that visual fatigue occurs in the eyeball E1, the controller 130 controls the massager 140 to massage peripheries of the eyeball E1. In practice, the massager 140 may be a different type of massager that may relieve the extraocular muscles surrounding the eyeball E1 of the user by using methods such as providing a heat range, shock, or pressure. In this embodiment, the massager 140 is a vibration assembly. The vibration frequency of the massager 140 is the same as the nystagmus frequency of the eyeball E1.

Figure 3:
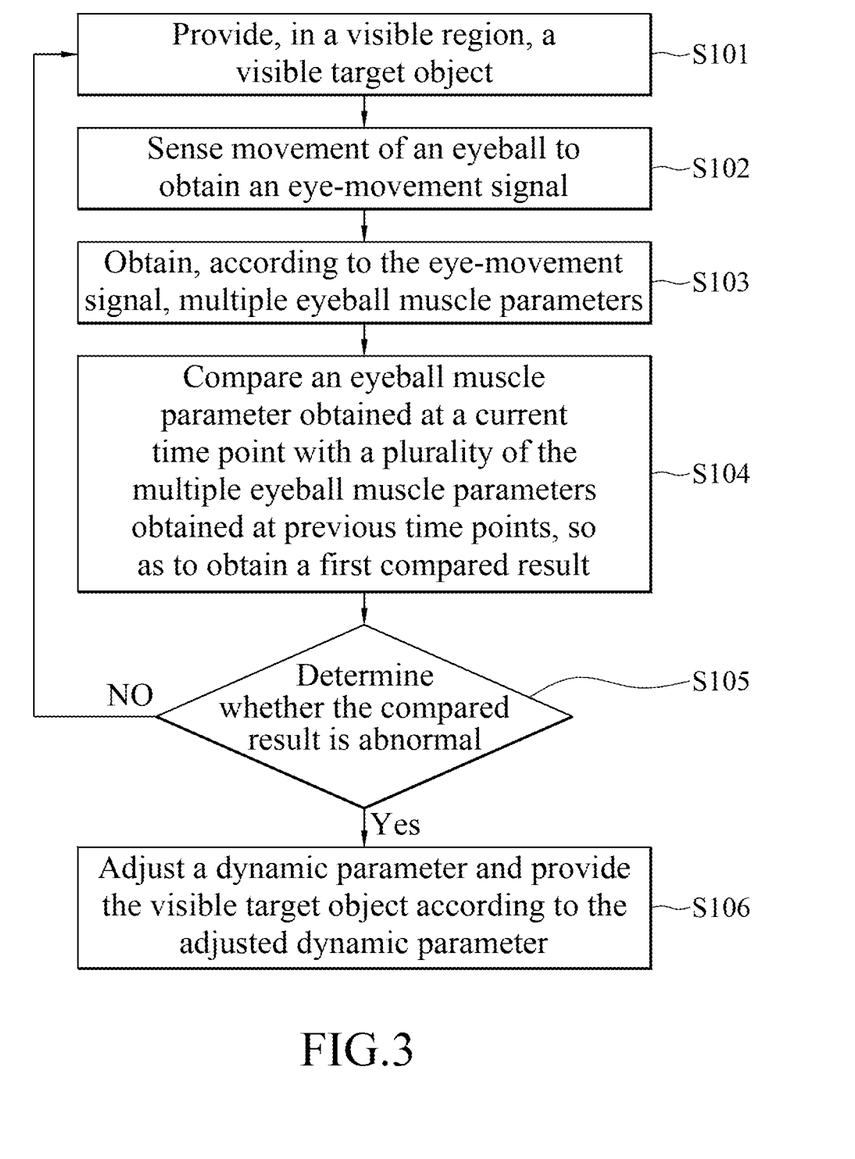
FIG. 3 is a schematic flowchart of a visual acuity (VA) training method according to an embodiment of the present invention.

FIG. 3 is a schematic flowchart of a visual acuity (VA) training method according to an embodiment of the present invention. Refer to FIG. 3 in combination with FIG. 1A, FIG. 1B, and FIG. 2A to FIG. 2D.

Step S101: When a user uses the visual acuity (VA) training device 100, the guiding unit 110 provides, in a visible region M1, a visible target object O1 according to a dynamic parameter, so as to guide an eyeball E1 of the user to move towards multiple predetermined positions P1, P2, P3, P4 for viewing the visible target object O1.

Step S102: The eye-movement sensor 120 senses movement of the eyeball E1 at different time points to obtain the corresponding eye-movement signals and transmits the sensed eye-movement signals to the controller 130.

Step S103: The controller 130 receives multiple eye-movement signals from the eye-movement sensor 120 and obtains, according to the eye-movement signals at the different time points, corresponding eyeball muscle parameters of one or more ocular muscles of the eyeball moving at the different time points. Thus, the user operates the visual acuity (VA) training device 100, so that the processing unit 134 may calculate, for measurement at each current time point, a historical basic value of at least some of eyeball muscle parameters at previous time points relative to the current time point.

Step S104: The processing unit 134 compares the eyeball muscle parameter obtained at each current time point with the historical basic value of at least some of the eyeball muscle parameters at the previous time points, so as to obtain a compared result corresponding to each current time point.

Step S105: The processing unit 134 determines whether the compared result is normal or abnormal, that is, the processing unit 134 analyzes whether the compared result is greater than or less than a preset threshold or does not fall within a preset interval of the historical basic value.

If it is determined that the compared result is abnormal (corresponding to the compared result being greater than or less than a preset threshold or not falling within a preset interval of the historical basic value at a certain time point), the processing unit 134 determines that movement of the eyeball E1 corresponding to the time point of the compared result is abnormal as compared with movement of the eyeball E1 movement at other time points and adjusts the dynamic parameter to be in a training mode. Accordingly, step S106 is performed. The processing unit 134 may accordingly adjust the dynamic parameter of the visible target object O1 according to the eyeball muscle parameter at the time point corresponding to the compared result, to enter the training mode, so as to intensively train the unbalanced ocular muscles according to the adjusted dynamic parameter. The compared result is determined based on being greater than or less than a threshold, depending on the type of the eyeball muscle parameter. For example, if the eyeball muscle parameter is the time and amplitude of eyeball saccade, the condition is set as being greater than a threshold. If the eyeball muscle parameter is a degree of stretching or contraction of an ocular muscle, the condition is set as being less than a threshold.

If it is determined that the compared result is normal (corresponding to the compared result being less than or greater than a preset threshold, or falling within a preset interval of the historical basic value at a certain time point), the processing unit 134 adjusts the dynamic parameter to be in a sensing mode. Step S102 is returned, and movement of the eyeball E1 is continuously sensed.

In other embodiments, the gradual increase in the compared value between the eyeball muscle parameter obtained at the current time point and a historical basic value of multiple eyeball muscle parameters obtained at previous time points calculated by the processing unit 134 indicates that the movement velocity or the movement direction of the eyeball E1 is gradually out of step with the movement velocity or the movement direction of the visible target object O1. Accordingly, the processing unit 134 determines that visual fatigue occurs in the eyeball E1. When visual fatigue occurs in the eyeball E1, a massager 140 is used to massage peripheries of the eyeball E1. In detail, when the processing unit 134 of the controller 130 determines that visual fatigue occurs in the eyeball E1, the controller 130 controls the massager 140 to massage peripheries of the eyeball E1. In this embodiment, the massager 140 is a vibration assembly. The vibration frequency of the massager 140 is the same as the nystagmus frequency of the eyeball E1.

In view of the above, the embodiments of the present invention provide a visual acuity (VA) training device and a training method thereof. The visual acuity (VA) training device includes a guiding unit, an eye-movement sensor, and a controller. An eyeball of a user moves towards multiple predetermined positions along with a visible target object of the guiding unit. The eye-movement sensor senses movement of the eyeball, so as to obtain multiple eye-movement signals. The controller calculates to obtain multiple corresponding eyeball muscle parameters based on the eye-movement signals.

A difference between the movement state of at least one eyeball of a user and the normal state indicates that the movement of ocular muscles of the eyeball is unbalanced. Specifically, the controller determines whether the movement of ocular muscles at a current time point is unbalanced by comparing an eyeball muscle parameter obtained at the current time point with a historical basic value. If the compared result between the eyeball muscle parameter obtained at the current time point and the historical basic value is greater than or less than a threshold or does not fall within a preset interval of the historical basic value (or referred to as a normal interval), it indicates that the movement of the eyeball at the time point corresponding to the compared result is abnormal as compared with the movement of the eyeball at previous time points. On the basis of this, the controller can carry out training with respect to unbalanced ocular muscles of the eyeball by adjusting the dynamic parameter of the visible target object. By the visual acuity (VA) training device and the visual acuity (VA) training method provided by the embodiments of the present invention, movement of ocular muscles can be adjusted with respect to a visual acuity (VA) situation of each person by changing predetermined positions of a visible target object in response to an individual visual acuity (VA) change.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A the visual acuity (VA) training device, wherein the visual acuity (VA) training device comprises:
   a guiding unit, configured to guide an eyeball to move towards multiple predetermined positions;
   an eye-movement sensor, configured to obtain multiple eye-movement signals according to movement of the eyeball; and
   a controller, configured to obtain multiple eyeball muscle parameters according to the multiple eye-movement signals, and the controller controlling the guiding unit according to the multiple eyeball muscle parameters, so as to adjust the predetermined positions,
   wherein the controller comprises a memory and a processing unit electrically connected to the memory, the multiple eye-movement signals are stored in the memory, and the processing unit analyzes the multiple eye-movement signals to obtain the multiple eyeball muscle parameters, wherein the processing unit calculates a compared result between each of the eyeball muscle parameters and a historical basic value of a plurality of the multiple eyeball muscle parameters, and the processing unit adjusts the predetermined positions according to a maximum value among the multiple compared results.

2. The visual acuity (VA) training device according to claim 1, wherein the eyeball muscle parameter comprises a movement vector of the eyeball.

3. The visual acuity (VA) training device according to claim 1, wherein if the multiple compared results between each of the eyeball muscle parameters and the historical basic value of multiple eyeball muscle parameters gradually become larger, the controller determines that visual fatigue occurs in the eyeball.

4. The visual acuity (VA) training device according to claim 3, wherein the visual acuity (VA) training device further comprises a massager, wherein if the controller determines that visual fatigue occurs in the eyeball, the controller controls the massager to massage peripheries of the eyeball.

5. The visual acuity (VA) training device according to claim 4, wherein the vibration frequency of the massager is the same as the nystagmus frequency of the eyeball.

6. A visual acuity (VA) training method, applicable for viewing by an eyeball of a user, wherein the method comprises:

providing, in a visible region, a visible target object according to a dynamic parameter;

sensing movement of the eyeball, so as to obtain an eye-movement signal;

obtaining multiple eyeball muscle parameters according to the eye-movement signal; and adjusting the dynamic parameter according to the eyeball muscle parameters, wherein the step of adjusting the dynamic parameter according to the multiple eyeball muscle parameters comprises:

calculating the eyeball muscle parameter obtained at each current time point and a historical basic value of a plurality of the multiple eyeball muscle parameters obtained at past time points;

calculating a compared result between the eyeball muscle parameter obtained at the current time point and the historical basic value; and judging the compared result, so as to adjust the dynamic parameter, wherein the step of judging the compared result, so as to adjust the dynamic parameter further comprises:

adjusting the dynamic parameter to be in a sensing mode if judging that the compared result is normal; and adjusting the dynamic parameter to be in a training mode if judging that the compared result is abnormal.

7. The visual acuity (VA) training method according to claim 6, wherein the eyeball muscle parameter comprises a movement vector of the eyeball.

8. The visual acuity (VA) training method according to claim 6, wherein the step of sensing the eye-movement signal comprises:

capturing an image of movement of the eyeball; and analyzing the image to obtain the eye-movement signal.

9. The visual acuity (VA) training method according to claim 6, comprising: determining that visual fatigue occurs in the eyeball if at least a plurality of the multiple compared results is gradually increased.

10. The visual acuity (VA) training method according to claim 9, wherein if determining that visual fatigue occurs in the eyeball, massaging peripheries of the eyeball by a massager.

11. A visual acuity (VA) training method, applicable for viewing by an eyeball of a user, wherein the method comprises:

providing, in a visible region, a visible target object according to a dynamic parameter;

sensing movement of the eyeball, so as to obtain an eye-movement signal;

obtaining multiple eyeball muscle parameters according to the eye-movement signal; and adjusting the dynamic parameter according to the eyeball muscle parameters, wherein the step of adjusting the dynamic parameter according to the multiple eyeball muscle parameters comprises:

calculating the eyeball muscle parameter obtained at each current time point and a historical basic value of a plurality of the multiple eyeball muscle parameters obtained at past time points;

calculating a compared result between the eyeball muscle parameter obtained at the current time point and the historical basic value;

judging the compared result, so as to adjust the dynamic parameter; and further comprising determining that visual fatigue occurs in the eyeball if at least a plurality of the multiple compared results is gradually increased, wherein if determining that visual fatigue occurs in the eyeball, massaging peripheries of the eyeball by a massage, and wherein a vibration frequency of the massager is the same as the nystagmus frequency of the eyeball.

* * * * *